United States Patent
Majeed et al.

(10) Patent No.: US 11,744,807 B2
(45) Date of Patent: Sep. 5, 2023

(54) THERAPEUTIC COMPOSITIONS AND METHODS FOR PULMONARY FIBROSIS

(71) Applicants: Muhammed Majeed, Bangalore (IN); Kalyanam Nagabhushanam, East Windsor, NJ (US); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 308 days.

(21) Appl. No.: 17/151,172

(22) Filed: Jan. 17, 2021

(65) Prior Publication Data
US 2021/0220291 A1 Jul. 22, 2021

Related U.S. Application Data

(60) Provisional application No. 62/962,343, filed on Jan. 17, 2020.

(51) Int. Cl.
*A61K 31/122* (2006.01)
*A61P 11/00* (2006.01)
*A61K 31/09* (2006.01)
*A61K 47/10* (2017.01)
*A61K 36/9066* (2006.01)

(52) U.S. Cl.
CPC ............ *A61K 31/122* (2013.01); *A61K 31/09* (2013.01); *A61K 36/9066* (2013.01); *A61K 47/10* (2013.01); *A61P 11/00* (2018.01)

(58) Field of Classification Search
CPC .................................................... A61K 31/122
See application file for complete search history.

(56) References Cited

PUBLICATIONS

Zhang et al., Curcumin's Metabolites, Tetrahydrocurcumin and Octahydrocurcumin, Possess Superior Anti-inflammatory Effects in vivo Through Suppression of TAK1-NF-kB Pathway, Frontiers in Pharmacology, Oct. 2018, vol. 9, Article 1181, pp. 1-12.*
Zhang 2, Antifibrotic effects of curcumin are associated with overexpression of cathepsins K and L in bleomycin treated mice and human fibroblasts, Respiratory Research 2011, 12:154, pp. 2-12.*
Schobert et al., Chemical and Biological Aspects of Garcinol and Isogarcinol: Recent Developments, Chem. Biodiversity, 2019, 16, e1900366, Wiley-VHCA AG.*
Zheng et al., Epigenetic Modulation of Collagen 1A1: Therapeutic Implications in Fibrosis and Endometriosis, Biology of Reproduction (2016) 94(4):87, 1-10.*

* cited by examiner

Primary Examiner — Svetlana M Ivanova

(57) ABSTRACT

The present invention discloses a method for therapeutic management of pulmonary fibrosis in mammals using a composition comprising iso-garcinol or octahydrocurcumin or a combination of iso-garcinol and octahydrocurcumin. The composition is very suitable for treating pulmonary fibrosis due to viral infections, specifically COVID 19 and for improving lung function during prognosis.

5 Claims, 4 Drawing Sheets

THERAPEUTIC COMPOSITIONS AND METHODS FOR PULMONARY FIBROSIS

CROSS-REFERENCE TO RELATED PATENT APPLICATIONS

This is a non-provisional US patent application claiming priority from U.S. Provisional application 62/962,343 filed on 17 Jan. 2020, the details of which are being incorporated herein by reference.

FILED OF INVENTION

The present invention relates to compositions for the management of pulmonary fibrosis. More specifically, the invention pertains to compositions comprising iso-garcinol and octahydrocurcumin for the management of pulmonary fibrosis.

BACKGROUND OF THE INVENTION

Pulmonary fibrosis ("scarring of the lungs") is a respiratory disease in which scars are formed in the lung tissues, leading to serious breathing problems. Scar formation, the accumulation of excess fibrous connective tissue (the process called fibrosis), leads to thickening of the walls, and causes reduced oxygen supply in the blood. As a consequence, patients suffer from perpetual shortness of breath.

There are over 200 types of pulmonary fibrosis, however, in most cases there is no definitive cause for its development. The most common type of pulmonary fibrosis is the Idiopathic pulmonary fibrosis (IPF) which has a no known cause. Pulmonary Fibrosis are also caused by different autoimmune diseases like rheumatoid arthritis, scleroderma or Sjogren's syndrome, viral infections, and gastroesophageal reflux disease (GERD). There are also familial cases of pulmonary fibrosis reported. Exposure to certain hazardous substances like asbestos, silica, cigarette smoke etc also increases the risk of pulmonary fibrosis. The signs and symptoms of pulmonary fibrosis include shortness of breath, particularly with exertion, chronic dry and hacking coughing, fatigue and weakness, chest discomfort including chest pain, loss of appetite, weight loss, aching joints and muscles, clubbing (widening and rounding) of the tips of the fingers or toes (Symptoms of pulmonary fibrosis, American lung association (lung.org/lung-health-diseases/lung-disease-lookup/pulmonaryfibrosis/introduction, last updated 27 Mar. 2020).

Recent evidence indicate that pulmonary fibrosis complicate infections caused by SARS-CoV-2, the causative agent for COVID 19 (A. Zumla et al., "Reducing mortality from 2019-nCoV: host-directed therapies should be an option," *The Lancet*, vol. 395, no. 10224, pp. e35-e36, 2020). Pulmonary fibrosis is a known sequela to ARDS, which is reported as one of the main cause for the development of severe COVID 19 condition (Vasarmidi et al., Pulmonary fibrosis in the aftermath of the Covid-19 era (Review), Exp Ther Med 20: 2557-2560, 2020). Thus, treating fibrosis in the aftermath of COVID 19 and ARDS is required for maintaining proper lung function.

There are different natural molecules that are currently being evaluated for the management of pulmonary fibrosis (Bahri et al., The efficacy of plant extract and bioactive compounds approaches in the treatment of pulmonary fibrosis: A systematic review, Biomedicine & Pharmacotherapy 93 (2017) 666-673; Impellizzeri et al., Protective effect of polyphenols in an inflammatory process associated with experimental pulmonary fibrosis in mice, British Journal of Nutrition (2015), 114, 853-865).

Curcumin from *Curcuma longa* has been reported to possess anti-fibrotic potential (Smith M R, et al. Curcumin inhibits fibrosis-related effects in IPF fibroblasts and in mice following bleomycin-induced lung injury. Am J Physiol Lung Cell Mol Physiol. 2010; 298:L616-L625). However, the plant also possesses other active metabolites of curcumin like tetrahydrocurcumin and octahydrocurcumin which possesses differential biological/therapeutic potential compared to curcumin. The potential of these metabolites in managing pulmonary fibrosis remain to be evaluated.

Similarly, Garcinol from *Garcinia* sp. has also been reported to reduce fibrosis (Hung et al. Protective effects of garcinol on dimethylnitrosamine-induced liver fibrosis in rats, Food Funct, 2014; 5(11):2883-91. doi: 10.1039/c4fo00342j). Another compound iso-garcinol, also reported to be present, which is structurally and biologically different from garcinol (N. Krishnamurthy, Y. S. Lewis, B. Ravindranath, On the structures of garcinol, iso-garcinol and camboginol, Tetrahedron Letters, Volume 22, Issue 8, 1981, Pages 793-796). The potential of iso-garcinol in managing the symptoms of pulmonary fibrosis is never reported or evaluated. The present invention discloses the potential of iso-garcinol and octahydrocurcumin in managing the symptoms of pulmonary fibrosis.

It is the principle object of the invention to disclose the use of iso-garcinol and octahydrocurcumin or their combination in therapeutic management of pulmonary fibrosis.

The present invention solves the above objective and provides further related advantages.

SUMMARY OF THE INVENTION

In a most preferred embodiment, the invention discloses a method for therapeutic management of pulmonary fibrosis in mammals, said method comprising step of administering a composition comprising iso-garcinol or octahydrocurcumin or a combination of iso-garcinol and octahydrocurcumin to mammals in need of such management to bring about a reduction in symptoms and features of pulmonary fibrosis.

Other features and advantages of the present invention will become apparent from the following more detailed description, taken in conjunction with the accompanying images, which illustrate, by way of example, the principle of the invention.

DESCRIPTION OF PREFERRED EMBODIMENTS

Figure 1:
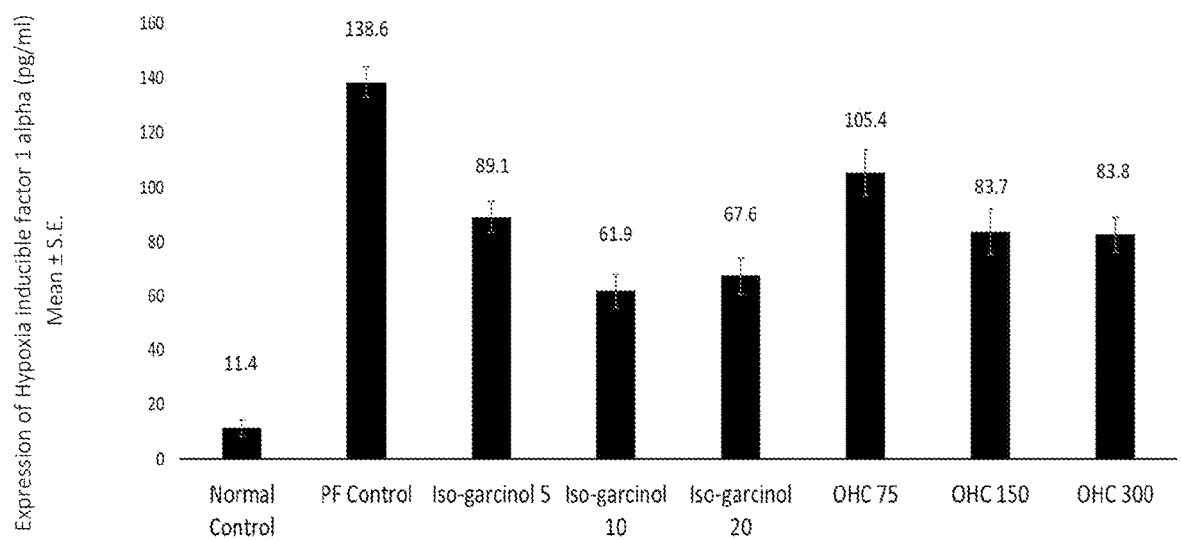
FIG. 1 is the graphical representation showing the dose dependent decrease in HIF-1α levels in rats with pulmonary fibrosis treated with varying doses (mg/kg bodyweight) of iso-garcinol and octahydrocurcumin (OHC) compared to normal and pulmonary fibrosis control groups.

In a most preferred embodiment, the invention discloses a method for therapeutic management of pulmonary fibrosis in mammals, said method comprising step of administering a composition comprising iso-garcinol or octahydrocurcumin or a combination of iso-garcinol and octahydrocurcumin to mammals in need of such management to bring about a reduction in symptoms and features of pulmonary fibrosis.

In another related embodiment, the symptoms of pulmonary fibrosis are selected from the group consisting of shortness of breath, chronic dry and hacking cough, fatigue and weakness, chest discomfort including chest pain, loss of appetite, weight loss, aching joints and muscles, clubbing of the tips of the fingers or toes. In yet another related embodiment, the features of pulmonary fibrosis include increased hypoxia, extracellular matrix generation and deposition of aberrant matrix, increased inflammation and influx of inflammatory markers, increased migration and proliferation of fibroblasts, increased mucus secretion and increased lung index. In yet another related aspect, the inflammatory markers are selected from the group consisting of TGF-β, IL-13, IL-1β, TNF-α, CCL-17. In another related embodiment, the mammal is human In another most preferred embodiment, the invention discloses a composition comprising iso-garcinol or octahydrocurcumin or a combination of iso-garcinol and octahydrocurcumin for use in the therapeutic management of pulmonary fibrosis in mammals. In a related embodiment, therapeutic management is brought about by a reduction in symptoms and features of pulmonary fibrosis.

In another related embodiment, the symptoms of pulmonary fibrosis are selected from the group consisting of shortness of breath, chronic dry and hacking cough, fatigue and weakness, chest discomfort including chest pain, loss of appetite, weight loss, aching joints and muscles, clubbing of the tips of the fingers or toes. In yet another related embodiment, the features of pulmonary fibrosis include increased hypoxia, extracellular matrix generation and deposition of aberrant matrix, increased inflammation and influx of inflammatory markers, increased migration and proliferation of fibroblasts, increased mucus secretion and increased lung index. In yet another related aspect, the inflammatory markers are selected from the group consisting of IL-13, IL-1β, TNF-α, CCL-17. In another related embodiment, the mammal is human The preferred embodiments of the invention are further described in the following illustrative examples.

Example 1: Bleomycin Induced Lung Fibrosis

After overnight fasting, the wistar rats were anesthetized (60 mg/kg ketamine HCl and 5 mg/kg xylazine) and a midline incision was made in the neck and the trachea was exposed. A tracheal cannula was inserted under direct visualization into the trachea. Pulmonary fibrosis was induced by intratracheal administration of single dose 0.1 mL of bleomycin (5 mg/kg in 0.9% NaCl). Treatment with the test material was given 5 min after administration of bleomycin for 14 consecutive days. After 14 days, BALF (bronchoalveolar lavage fluid) was obtained. Lung tissue was weighed to determine the lung index. Lung homogenate was stored at −80° C. for analysis of bio-markers. (Yildirim A, Ersoy Y, Ercan F et al., "Phosphodiesterase-5 inhibition by sildenafil citrate in a rat model of bleomycin-induced lung fibrosis," Pulmonary Pharmacol Therap. 2101; 23(3):215-221; Chen L, Wang T, Wang X et al., "Blockade of advanced glycation end product formation attenuates bleomycin-induced pulmonary fibrosis in rats," Respiratory Res. 2009; 10:55; Nergiz et al., The Protective Effect of Naringin against Bleomycin-Induced Pulmonary Fibrosis in Wistar Rats. Pulmonary Med. 2016, 12 p, http://dx.doi.org/10.1155/2016/7601393)

The rats were divided into the following groups:

TABLE 1

Grouping

| Group | Description |
| --- | --- |
| Group 1 | Normal control |
| Group 2 | Pulmonary fibrosis control - Bleomycin treated |
| Group 3 | Bleomycin + isogarcinol administered at 5 mg/kg bodyweight |
| Group 4 | Bleomycin + isogarcinol administered at 10 mg/kg body weight |
| Group 5 | Bleomycin + isogarcinol administered at 25 mg/kg bodyweight |
| Group 6 | Bleomycin + OHC administered at 75 mg/kg bodyweight |
| Group 7 | Bleomycin + OHC administered at 150 mg/kg bodyweight |
| Group 8 | Bleomycin + OHC administered at 300 mg/kg bodyweight |
| Group 9 | Bleomycin + isogarcinol administered at 10 mg/kg body weight + OHC administered at 150 mg/kg bodyweight |

For clarity the definition of the compounds administered in the above group is provided below:
OHC—octahydrocurcumin (pure compound)

The iso-garcinol and octahydrocurcumin used in the experiments were procured from Sami Labs Limited, Bangalore, India.

Quantitation of Biochemical Markers

The lung of the animals was removed and rinsed with ice-cold isotonic saline. To the tissues was added 4 ml/g tissue of extraction buffer containing 1 mM phenylmethylsulfonyl fluoride, 1 mg/ml aprotinin and 0.05% Tween 20 in phosphate buffered saline. Tissues were homogenized on ice with a polytron and the homogenate was centrifuged at 5000 g for 15 min. Aliquots of the supernatant were separated and used for biochemical analysis. Supernatants were stored at −80° C. until cytokine analysis (Pandey et al., Multifunctional neuroprotective effect of Withanone, a compound from *Withania somnifera* roots in alleviating cognitive dysfunction. Cytokine 102 (2018) 211-221). The levels of HIF-1 alpha, TGF-β, IL-13, IL-1β, TNF-α, CCL-17, osteopontin and mucin in the lung tissue homogenate was determined using methods and protocols already reported in scientific literature.

Determination of Effective Dose

Different concentration of iso-garcinol (5, 10, 20 mg/kg bodyweight) and octahydrocurcumin were first administered to rats and the effect of the compounds in reducing hypoxia related HIF-α was evaluated. Isogarcinol showed better reduction of HIF-α at 10 mg/kg bodyweight and octahydrocurcumin showed improved reduction at 150 mg/kg bodyweight (FIG. 1). Thus, iso-garcinol at 10 mg/kg bodyweight and octahydrocurcumin at 150 mg/kg bodyweight was used for the further combination studies.

Hypoxia

Hypoxia is a condition where not enough oxygen makes it to the cells and tissues in the body. This can happen even though blood flow is normal. It can lead to many serious, sometimes life-threatening complications. Hypoxia Inducible factor (HIF-1) signalling pathway is activated in inflammatory signalling and metabolic stress conditions, leading to hypoxia, increased extracellular matrix formation, futile angiogenesis and pulmonary hypertension resulting in fibrosis. Recent evidence indicate that hypoxia is a primary pathophysiologic feature and main cause of mortality in patients with severe COVID-19 and it accompanies all the stages of the disease. The protein targets of HIF-1α are involved in the severe hypoxia-induced activation of proinflammatory cytokine expression and the subsequent inflammation process and cytokine storm phase of COVID-19.

Figure 2:
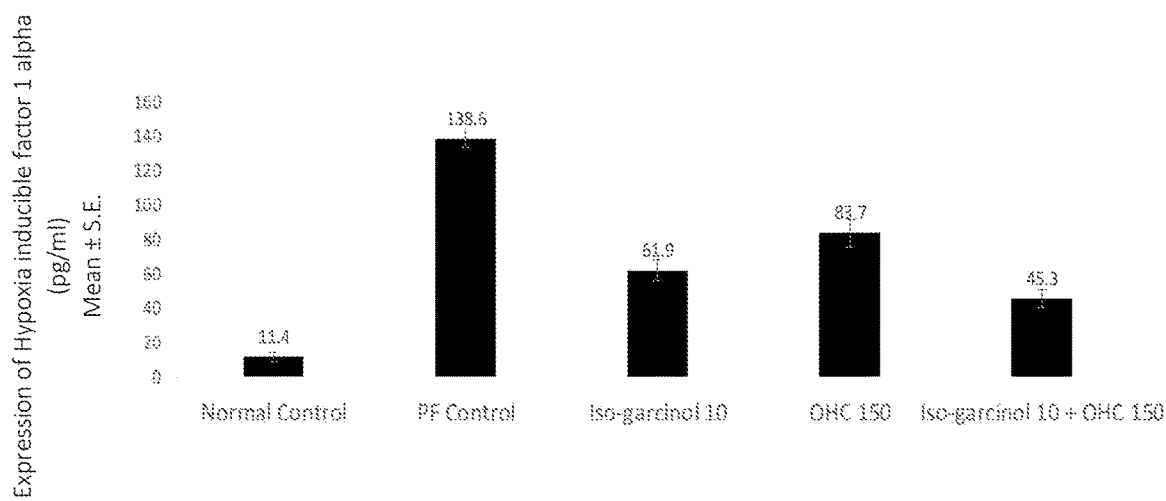
FIG. 2 is the graphical representation showing the decrease in HIF-1α levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

In the present study, compared to the control group (138.6 pg/ml) rats treated with iso-garcinol at 10 mg/kg bodyweight showed 55% reduction in HIF-α levels (61.9 pg/ml) and rats treated with octahydrocurcumin at 150 mg/kg bodyweight showed 36.6% reduction in HIF-α levels (83.7 pg/ml). The combination of iso-garcinol and octahydrocurcumin showed better reduction (67%—with value being 45.3 pg/ml) showing that both iso-garcinol and octahydrocurcumin, individually and in combination is very effective in reducing hypoxia (FIG. 2).

Transforming Growth Factor Beta in Pulmonary Fibrosis

TGF-β is one of the most potent inducers of extra cellular matrix production, including collagen and other matrix proteins. Its expression is elevated in both animal models of lung fibrosis and in fibrotic human lungs. In animal models of lung fibrosis, elevation of TGF-β expression precedes collagen synthesis and deposition. Deficiency in Smad3, a key TGF-β specific intracellular signaling molecule, attenuates lung fibrosis in response to bleomycin and to lung specific TGF-β1 over-expression (Yue, Xinping et al. "TGF-β: Titan of Lung Fibrogenesis." Curr Enzym Inhib. 2010 Jul. 1; 6(2): 10.2174/10067).

Figure 3:
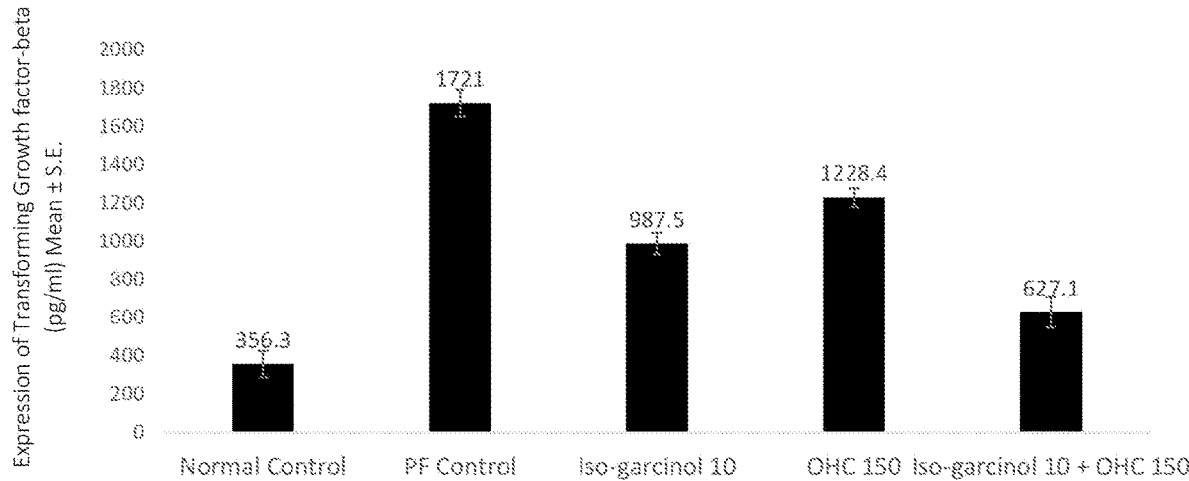
FIG. 3 is the graphical representation showing the decrease in TGF-β levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

In the present study, compared to the control group (1721 pg/ml) rats treated with iso-garcinol at 10 mg/kg bodyweight showed 42.62% reduction in TGF-β levels (987.5 pg/ml) and rats treated with octahydrocurcumin at 150 mg/kg bodyweight showed 28.62% reduction in TGF-β levels (1228.4 pg/ml). The combination of iso-garcinol and octahydrocurcumin showed better reduction (63.56%—627.1 pg/ml) (FIG. 3).

Collagen I in Pulmonary Fibrosis

In Pulmonary fibrosis, there is destruction of the normal architecture with the appearance of inflammatory cells and connective tissue components, particularly collagen in Pulmonary Fibrosis. Biochemical evidence exists suggesting increased deposition of collagen in patients with both acute and chronic forms of pulmonary fibrosis. There exist evidence for the production of type III collagen in the early active phase of disease with a preponderance of type I collagen in the late stages. Thus collagen 1 play a major role in the extracellular matrix formation.

In the present study, both iso-garcinol and octahydrocurcumin, individually and in combination was very effective in reducing collagen 1 (Table 2)

TABLE 2

Collagen 1 levels in rats treated with isogarcinol and octohydrocurcumin

| Group | Collagen-I (µg/ml) |
| --- | --- |
| Normal control | 64.25 ± 4.98 |
| Pulmonary Fibrosis control (Bleomycin, 5 mg/kg), intra-tracheal | 102.43 ± 3.70 |
| Isogarcinol 10 mg/kg p.o. | 89.68 ± 3.23 |
| Octahydrocurcumin 150 mg/kg | 95.56 ± 4.90 |
| Isogarcinol 10 mg/kg + Octahydrocurcumin 150 mg/kg | 75.68 ± 3.45 |

Both iso-garcinol and octahydrocurcumin was effective in preventing ECM formation by reducing collagen 1 and TGF-β.

Inflammatory Markers in Pulmonary Fibrosis

Multiple cell types are found at sites of lung fibrosis. Many are direct producers of extracellular matrix (ECM), or indirectly promote the generation and deposition of aberrant matrix. Both T cells and alternatively activated macrophages express IL-13 in the pulomonary fibrosis lung. Both of these cell types are found in increased numbers in IPF. Similarly TNFα and IL-1β levels are also elevated.

The development of pulmonary fibrosis is a Th2-mediated process. Chemokines that are associated with a Th2 profile (CCL17 and CCL22) have an important role in the development of pulmonary fibrosis. Neutralization of CCL17, but not CCL22, led to a reduction in pulmonary fibrosis. Immunolocalization of bleomycin-treated lung tissue and human idiopathic pulmonary fibrosis tissue specimens showed that epithelial cells expressed CCL17. Study demonstrates a central role for Th2 chemokines and the macrophage in the pathogenesis of pulmonary fibrosis and are further support for the role of a Th2 phenotype in the pathogenesis of pulmonary fibrosis. These chemokines and their receptor, namely CCR4, are elevated in areas of fibrotic lung tissue as compared with normal pulmonary parenchyma.

Figure 4:
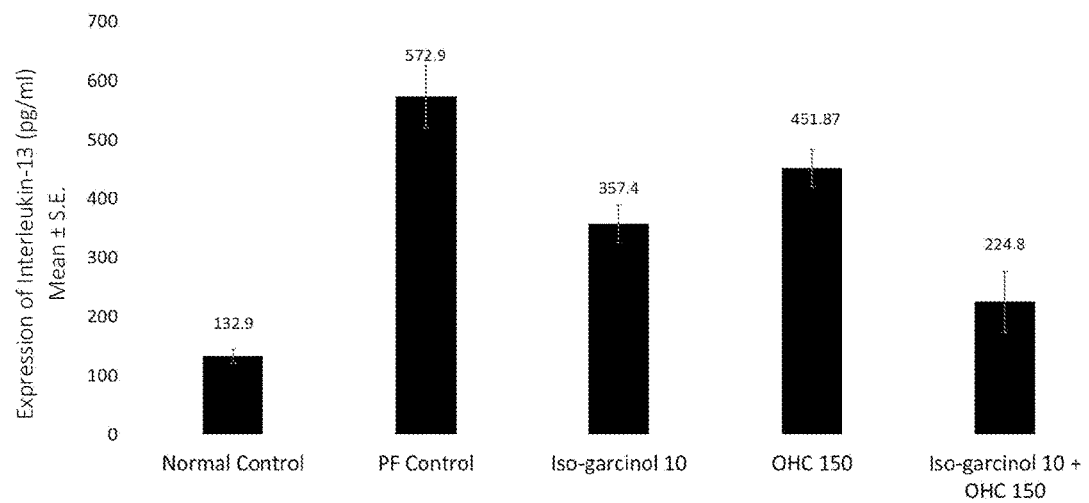
FIG. 4 is the graphical representation showing the decrease in IL-13 levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.
Figure 5:
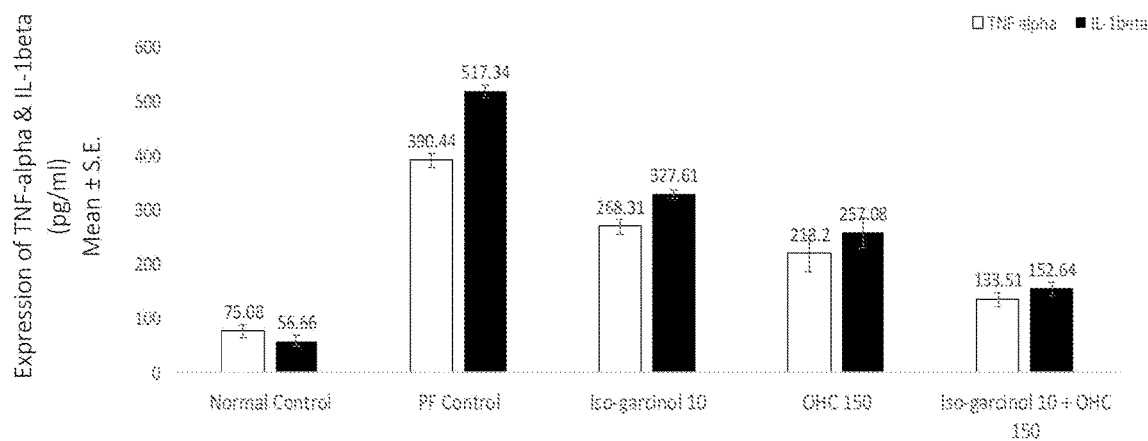
FIG. 5 is the graphical representation showing the decrease in TNF-α AND IL-1β levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

In the present study, the levels of inflammatory markers IL-13 (FIG. 4), TNF-α & IL-1β (FIG. 5) were significantly reduced by iso-garcinol and octahydrocurcumin thereby preventing inflammation and generation and deposition of aberrant matrix.

Figure 6:
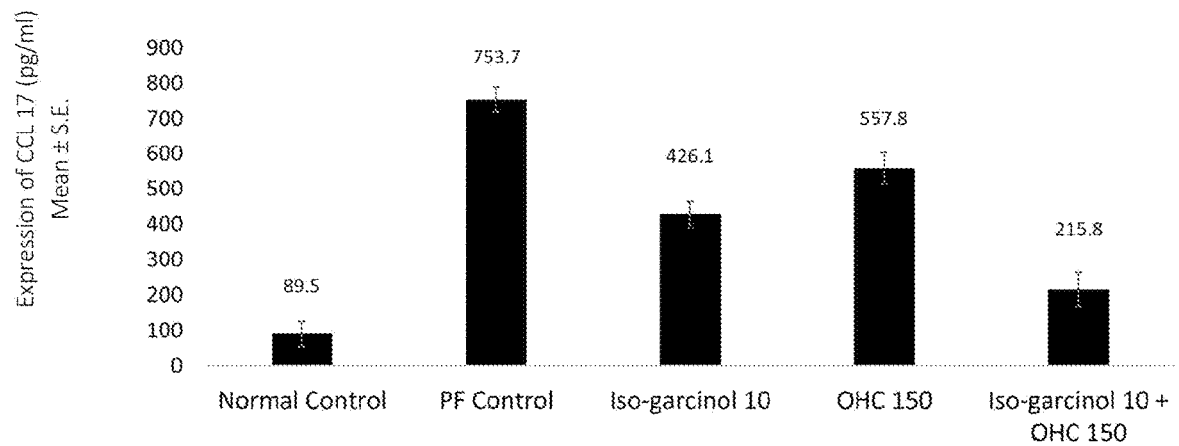
FIG. 6 is the graphical representation showing the decrease in CCL-17 levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

Isogarcinol and octahydrocurcumin also reduced the levels of chemokine CCL-17 (FIG. 6) indicating that they can prevent the inflammatory upsurge and "cytokine storm" which are reported as the clinical features of viral infections like COVID 19.

Osteopontin in Lung Fibrosis

Figure 7:
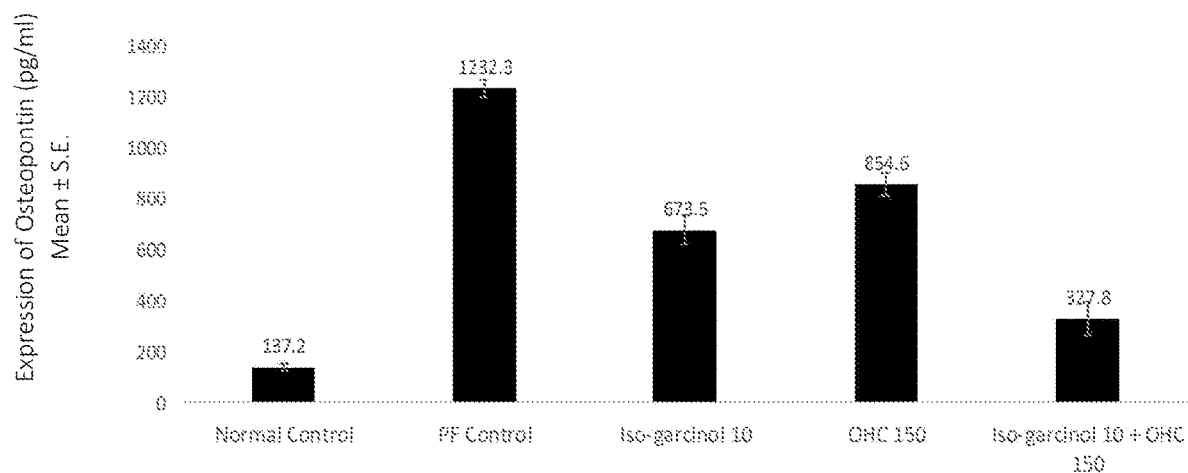
FIG. 7 is the graphical representation showing the decrease in osteoponin levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

Osteopontin is localized to alveolar epithelial cells in fibrosis lungs and also significantly elevated in bronchoalveolar lavage from pulmonary fibrosis patients. Osteopontin induces a significant increase of migration and proliferation in both fibroblasts and epithelial cells. In the present study isogarcinol and octahydrocurcumin also reduced the levels of osteopontin (FIG. 7), thereby indicating that they are very effective in preventing migration and proliferation of fibroblasts.

Mucin in Lung Fibrosis

In the normal lungs, mucus is responsible for trapping inhaled particles, including bacteria, and transporting them out of the airways by ciliary and cough-driven forces. Mucins, the glycosylated proteins in mucus, are primarily responsible for giving mucus their viscoelastic properties. The overproduction of a lung mucin (MUC5B) has consistently been shown to be the strongest risk for the development of idiopathic pulmonary fibrosis. Findings suggest that targeting MUC5B in the terminal airways of patients with preclinical stages of interstitial lung disease represents a strategy to prevent the progression of preclinical pulmonary fibrosis.

Figure 8:
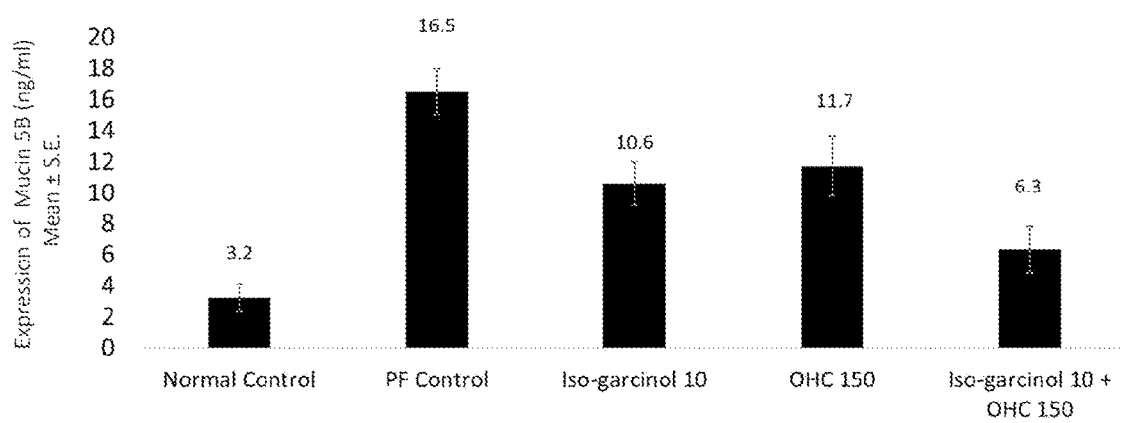
FIG. 8 is the graphical representation showing the decrease in mucin 5B levels in rats with pulmonary fibrosis treated with 10 mg/kg bodyweight of iso-garcinol and 150 mg/kg bodyweight of octahydrocurcumin (OHC) individually and in combination, compared to normal and pulmonary fibrosis control groups.

In the present study isogarcinol and octahydrocurcumin also reduced the levels of MUC 5B (FIG. 8), thereby indicating that they are very effective in preventing mucus formation.

Lung Index

Lung index calculated using the below formula

Lung Index=(weight of the lung/bodyweight)×100

The lung index in the control group with pulmonary fibrosis was high due the deposition and increase in fibrotic tissue. Isogarcinol and octahydrocurcumin decreased the lung index (Table 3), indicating the reduction in the fibrosis and accumulation of extracellular matrix in the lungs.

TABLE 3

| Lung index | |
| --- | --- |
| Group | Lung index |
| Normal control | 0.75 ± 0.053 |
| Pulmonary Fibrosis control (Bleomycin, 5 mg/kg), intra-tracheal | 1.39 ± 0.034 |
| Isogarcinol 10 mg/kg p.o. | 1.19 ± 0.035 |
| Octahydrocurcumin 150 mg/kg | 1.02 ± 0.045 |

TABLE 3-continued

| Lung index | |
| --- | --- |
| Group | Lung index |
| Isogarcinol 10 mg/kg + Octahydrocurcumin 150 mg/kg | 0.83 ± 0.062 |

Overall, the results suggest both iso-garcinol and octahydrocurcumin individually and in combination is very effective in managing pulmonary fibrosis by reducing hypoxia, preventing extracellular matrix formation and generation/deposition of aberrant matrix, reducing inflammation and preventing inflammation upsurge, preventing migration and proliferation of fibroblasts, preventing mucus secretion and reducing the lung index. The composition is very suitable for treating COPD and ARDS due to viral infections, specifically COVID 19 and for improving lung function during prognosis.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method for therapeutic management of pulmonary fibrosis in a mammal in need thereof, said method comprising the step of administering a composition comprising isogarcinol or a combination of isogarcinol and octahydrocurcumin to the mammal to bring about a reduction in symptoms and features of pulmonary fibrosis.

2. The method of claim 1, wherein the symptoms of pulmonary fibrosis are selected from the group consisting of shortness of breath, chronic dry and hacking cough, fatigue and weakness, chest discomfort, chest pain, loss of appetite, weight loss, aching joints and muscles, clubbing of the tips of the fingers or toes.

3. The method of claim 1, wherein the features of pulmonary fibrosis include increased hypoxia, extracellular matrix generation and deposition of aberrant matrix, increased inflammation and influx of inflammatory markers, increased migration and proliferation of fibroblasts, increased mucus secretion and increased lung index.

4. The method of claim 3, wherein the inflammatory markers are selected from the group consisting of TGF-$\beta$, IL-13, IL-1$\beta$, TNF-$\alpha$, CCL-17.

5. The method as in claim 1, wherein the mammal is human.

* * * * *